(12) United States Patent
Genio et al.

(10) Patent No.: US 8,027,031 B2
(45) Date of Patent: *Sep. 27, 2011

(54) SPECTROMETRIC METROLOGY OF WORKPIECES USING A PERMANENT WINDOW AS A SPECTRAL REFERENCE

(75) Inventors: Edgar Genio, Santa Clara, CA (US); Edward W. Budiarto, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/025,064

(22) Filed: Feb. 10, 2011

(65) Prior Publication Data

US 2011/0130995 A1   Jun. 2, 2011

Related U.S. Application Data

(63) Continuation of application No. 12/388,222, filed on Feb. 18, 2009, now Pat. No. 7,911,603.

(60) Provisional application No. 61/197,267, filed on Oct. 23, 2008.

(51) Int. Cl.
*G01J 3/42* (2006.01)

(52) U.S. Cl. ........................................ 356/300; 356/326

(58) Field of Classification Search .................. 356/300, 356/326, 328
See application file for complete search history.

(56) References Cited

U.S. PATENT DOCUMENTS

| 3,992,100 A | 11/1976 | Lodzinski et al. ............... 356/73 |
| 7,911,603 B2 * | 3/2011 | Genio et al. ................... 356/300 |
| 2010/0106444 A1 | 4/2010 | Genio et al. ..................... 702/85 |

OTHER PUBLICATIONS

Official Action Dated Sep. 28, 2010 Issued in Co-Pending U.S. Appl. No. 12/388,222.
Official Action Dated Dec. 2, 2010 Issued in Co-Pending U.S. Appl. No. 12/388,222.

\* cited by examiner

*Primary Examiner* — F. L. Evans
(74) *Attorney, Agent, or Firm* — Robert M. Wallace

(57) ABSTRACT

In a spectrographic workpiece metrology system having an optical viewing window, the viewing window is calibrated against a reference sample of a known absolute reflectance spectrum to produce a normalized reflectance spectrum of the reference sample, which is combined with the absolute reflectance spectrum to produce a correction factor. Successive production workpieces are measured through the window and calibrated against the viewing window reflectance, and transformed to absolute reflectance spectra using the same correction factor without having to re-load the reference sample.

17 Claims, 9 Drawing Sheets

US 8,027,031 B2

SPECTROMETRIC METROLOGY OF WORKPIECES USING A PERMANENT WINDOW AS A SPECTRAL REFERENCE

CROSS-REFERENCE TO RELATED APPLICATIONS

This application is a continuation of U.S. patent application Ser. No. 12/388,222 filed Feb. 18, 2009 entitled SPECTROMETRIC METROLOGY OF WORKPIECES USING A PERMANENT WINDOW AS A SPECTRAL REFERENCE By Edgar Genio, et al. now U.S. Pat. No. 7,911,603, which claims the benefit of U.S. Provisional Application Ser. No. 61/197,267, filed Oct. 23, 2008. All of the above applications are hereby incorporated by reference in their entirety.

BACKGROUND

Various surface properties of an integrated circuit or wafer are determined in a metrology system from the spectrum of light reflected from the integrated circuit surface. The spectrum of reflected light is referred to herein as the spectral reflectance or, equivalently, the reflectance spectrum. One surface property of interest, for example, is thin film thickness. Another property may be the length or height of a periodic structural features. The reflected light is collected and dispersed by a wavelength separation element, such as a diffraction grating. The wavelength dispersed image or spectrum obtained from the diffraction grating represents a distribution of light intensity across a wavelength range. This distribution is processed in accordance with conventional algorithms to produce a measurement of the surface property of interest. In order for such processing to produce valid results, the distribution or spectrum must represent the absolute reflectance spectrum of the integrated circuit surface. The light source used to generate the spectrum may itself have a non-uniform intensity distribution across the wavelength range, which distorts the measured reflectance spectrum of the integrated circuit surface, thereby preventing observation of the absolute reflectance spectrum. Furthermore, the spectral distribution and intensity of the light source may drift over time. In order to solve these problems, the conventional approach is to periodically replace the integrated circuit or production wafer with a reference sample whose absolute reflectance spectrum has been predetermined. The metrology system then measures the spectral reflectance of the reference sample. The measured reflectance of the reference sample is then compared with its predetermined absolute reflectance spectrum, to generate a correction function. This correction function accounts for non-uniformity in the light source spectrum and for light source drift. The correction function is then applied to the observed spectral reflectance of the production wafer to produce the absolute reflectance of the production wafer. This absolute reflectance is then processed to compute the true measure of the surface property of interest.

One limitation of the foregoing approach is that a series of production wafer measurements is followed by the measurement of a reference sample, in order to frequently generate a new correction function to guard against system drift. For each such reference sample measurement, a reference sample must replace a production wafer on the metrology system wafer support, which greatly reduces productivity. What is needed is a metrology system that does not require the periodic replacement of a production wafer with a reference sample, but which nevertheless guards against system drift.

SUMMARY OF THE INVENTION

In a spectrographic workpiece or wafer metrology system having an optical viewing window, the viewing window is calibrated against a reference sample of a known absolute reflectance spectrum to produce a normalized reflectance spectrum of the reference sample, which is combined with the absolute reflectance spectrum to produce a correction factor. Successive production workpieces are measured through the window and calibrated against periodic measurements of the viewing window reflectance, and transformed to absolute reflectance spectra using the same correction factor without having to re-load the reference sample.

In one embodiment, a method is provided for measuring the absolute reflectance spectrum of a workpiece using an optical sensing apparatus having a viewing window facing a workpiece support surface. The method includes obtaining a reflectance spectrum of the viewing window and then measuring through the viewing window a reflectance spectrum of a reference sample having a predetermined absolute reflectance spectrum. The measured reflectance spectrum of the reference sample is then normalized with the reflectance spectrum of the window. A correction factor is then computed by combining the absolute reflectance spectrum and the normalized reflectance spectrum of the reference sample. Thereafter, for each one of a succession of production workpieces to be measured, the reflectance spectrum of a successive one of the production workpieces is measured through the window. The method further includes normalizing the production workpiece reflectance spectrum with the viewing window reflectance spectrum, and computing the production workpiece absolute reflectance spectrum by combining the normalized production workpiece reflectance spectrum with the correction function.

BRIEF DESCRIPTION OF THE DRAWINGS

So that the manner in which the exemplary embodiments of the present invention are attained and can be understood in detail, a more particular description of the invention, briefly summarized above, may be had by reference to the embodiments thereof which are illustrated in the appended drawings. It is to be appreciated that certain well known processes are not discussed herein in order to not obscure the invention.

FIGS. 4A-4C are graphs of functions obtained or used in the embodiment of FIG. 3, of which FIG. 4A depicts a reflectance spectrum of a reference sample, FIG. 4B depicts the absolute reflectance spectrum of the reference sample, and FIG. 4C depicts a correction function obtained from a combination of the reflectance spectra of FIGS. 4A and 4B.

FIGS. 6A through 6I depict various distributions of light intensity as functions of wavelength that are obtained or used in the method of FIGS. 5A and 5B, of which:

FIG. 6A is a graph of the measured reflectance spectrum of the viewing window.

FIG. 6B is a graph of the measured reflectance spectrum of a reference sample obtained through the viewing window.

FIG. 6C is a graph of a normalized reflectance spectrum of the reference sample obtained by combining the functions of FIGS. 6A and 6B.

FIG. 6D is a graph of a difference reflectance spectrum computed from the spectrum of FIG. 6C.

FIG. 6E is a graph of a correction function computed from a combination of the difference spectrum of FIG. 6D and a predetermined absolute reflectance spectrum of the reference sample.

FIG. 6F is a graph of the reflectance spectrum of a production workpiece measured through the viewing window.

FIG. 6G is a graph of a normalized reflectance spectrum of the production workpiece obtained by combining the functions of FIGS. 6A and 6F.

FIG. 6H is a graph of a difference reflectance spectrum computed from the spectrum of FIG. 6G.

FIG. 6I is a graph of the absolute reflectance spectrum of the production workpiece obtained by combining the functions of FIGS. 6H ad 6E.

Figure 1:
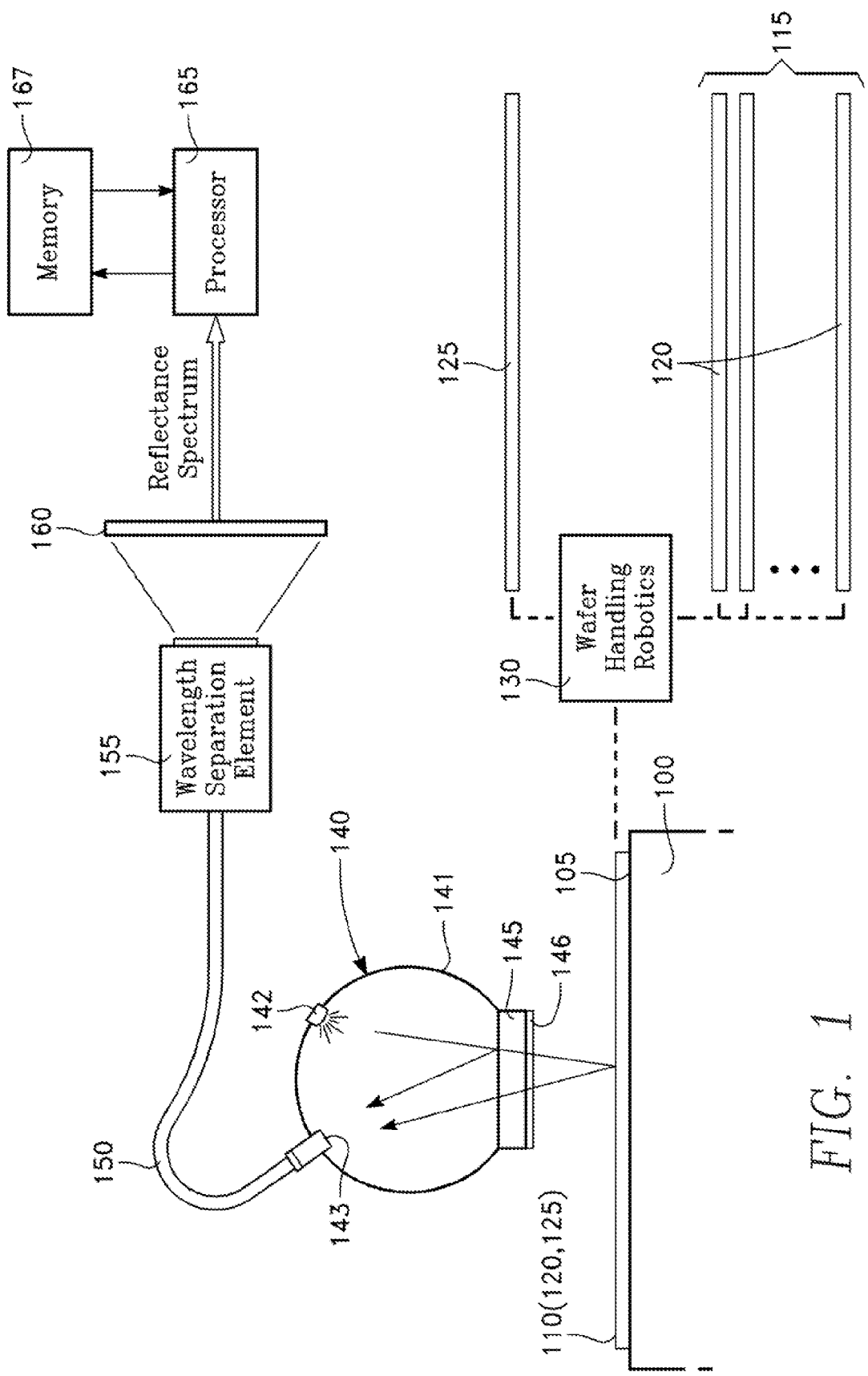
FIG. 1 is a schematic diagram of a workpiece metrology system in accordance with one embodiment.

To facilitate understanding, identical reference numerals have been used, where possible, to designate identical elements that are common to the figures. It is contemplated that elements and features of one embodiment may be beneficially incorporated in other embodiments without further recitation. It is to be noted, however, that the appended drawings illustrate only exemplary embodiments of this invention and are therefore not to be considered limiting of its scope, for the invention may admit to other equally effective embodiments.

DETAILED DESCRIPTION

FIG. 1 depicts a workpiece metrology system in accordance with one embodiment. A workpiece support 100 having a support surface 105 holds a workpiece 110 which may be either a production workpiece or wafer taken from a stack 115 of production workpieces 120 or may be a reference sample 125 taken from a holding location. The workpiece may be a semiconductor wafer of individual die having integrated circuit features, or a display or a solar panel or a coated glass or a photolithographic mask, for example. A workpiece handling robotic apparatus 130 or conveyor rollers transfers a production workpiece 120 or the reference sample 125 from or to the support 100. The conveyor rollers or the robot can themselves be the support for the workpiece. The absolute reflectance spectrum of the reference sample 125 has been previously determined under ideal laboratory conditions and is known to the workpiece metrology system. An optical sensing apparatus 140 collects light reflected from the workpiece 110 from which the reflectance spectrum of the workpiece 110 is measured. The metrology system necessarily has some non-uniform spectral response that distorts the measured reflectance spectrum. As discussed above, this may be attributable to a non-uniform spectrum of the light source employed by the optical apparatus 140, or to drift in the light source, or to the spectral response of components of the optical apparatus 140. In order to determine a spectral correction function for that distortion, the reference sample 125 is placed on the support 100 and is scanned by the optical apparatus 140 to determine its measured reflectance spectrum. The metrology system determines the required correction function by comparing the measured reflectance spectrum of the reference sample with its predetermined absolute reflectance spectrum. The reference sample 125 is then removed from the support 100 and one of the production workpieces 120 is placed on the support 100 to obtain a measured reflectance spectrum of the production workpiece 120. The absolute reflectance spectrum of the production workpiece 120 is then obtained by combining the measured reflectance spectrum of the production workpiece 120 with the spectral correction function previously obtained using the reference sample 125. A succession of the production workpieces 120 may be measured in this manner. However, since the metrology system or its light source may drift, the procedure must be interrupted by replacing the current production workpiece 120 on the support 100 with the reference sample 125, so that a new correction function may be obtained in preparation for the measuring the next production workpiece. This interruption represents a significant hindrance to productivity.

We have discovered a way of obtaining the absolute reflectance spectrum of the stack 115 of production workpieces 120 free of the distortion referred to above without having to periodically place the reference sample 125 on the support 100. In one embodiment, a viewing window 145 of the optical apparatus 140 serves as a permanent secondary reference sample to provide on-going correction against system drift. Initially, the viewing window 145 is calibrated against the reference sample 125 to provide a fixed correction factor. The reference sample 125 is then removed from the support 100 to make way for the succession of production workpieces 120 to be placed on the support 100. Secondary corrections for system drift are determined by periodically detecting changes in the apparent reflectance spectrum of the viewing window 145 by itself. The most recent secondary correction is combined with the correction function to provide an up-to-date correction function which transforms the measured reflectance spectrum of the latest production workpiece to the absolute reflectance spectrum. One advantage is that the reference sample 125 is not placed on the support 100 to periodically check for system drift. The periodic check and correction for system drift is performed by simply obtaining the reflectance spectrum of the viewing window 145 by itself. Specifically, a measurement is performed in such a manner that the only light returned to the sensor is that which is reflected from the viewing window 145. This may be done periodically after the processing or measurement of a predetermined number of production wafers. No reference sample need be loaded to perform this check, so that throughout most of the cycle, only the production workpieces 120 are loaded onto the support 100. By thus loading the stack 115 of production workpieces 120 onto the support 100 one at a time without having to load the reference sample 125, productivity of the metrology system is significantly increased. Measurement of the viewing window reflectance spectrum may be made by either removing any workpiece from the support 100 (provided the support 100 has little or no reflectance) or, if the workpiece is of the type transported by rollers, the measurement may be made between rollers, for example.

The optical apparatus 140 of FIG. 1 may be implemented, in one embodiment, as a reflecting hollow sphere 141 containing a light source 142 and a light receiver 143. The light receiver 143 may be the termination of a fiber optic cable, for example. The interior surface of the hollow sphere 141 is reflective. The hollow sphere 141 includes a viewing window 145 facing the support 100. The window 145 may be formed of a partially material such as glass. In one embodiment, a film or coating 146 of an optically reflective material may be placed on the viewing window 145 to enhance its reflectivity. A fiber optic cable 150 conducts the light collected at the light receiver 143 to a wavelength separation element 155, which may be a diffraction grating or a prism that disperses the light into a spectrum. An image sensor 160 captures the spectrum as a digital image, which is processed by a processor 165. The processor 165 is provided with a memory 167 which may store the predetermined absolute reflectance spectrum of the reference sample 125.

In embodiments described below, it is necessary to periodically obtain the reflectance spectrum of the viewing window 145 by itself in the absence of any production workpiece or reference sample on the support 100. For this purpose, the top surface of the support 100 may an optically absorbing layer which reflects no light or reflects only a negligible amount of light. As a result, in the absence of any workpiece 110 on the support 100, the only light detected at the light receiver 143 is light reflected from the viewing window 145.

Figure 2:
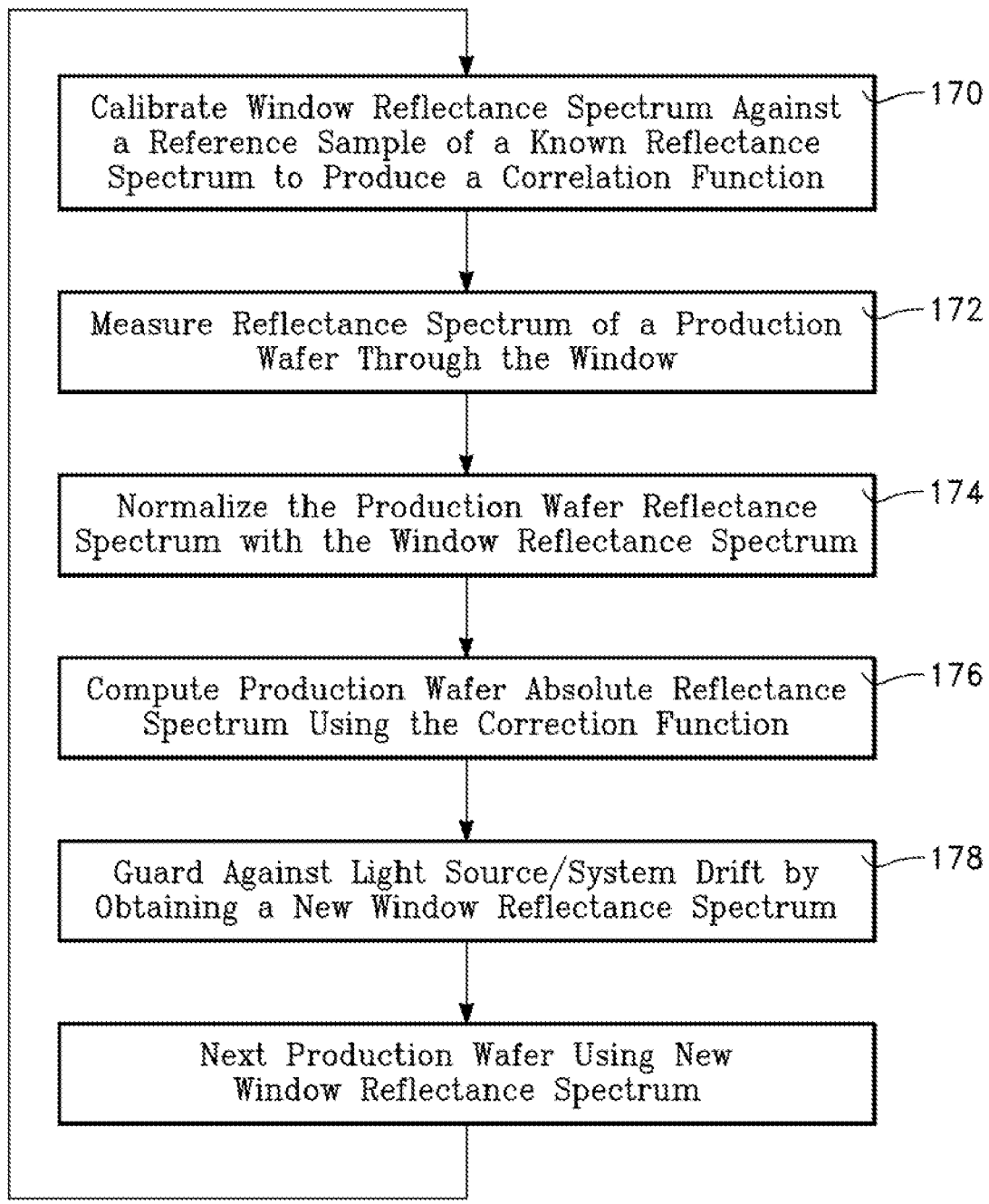
FIG. 2 is a block diagram representing a simplified overview of a method in accordance with an embodiment.

FIG. 2 is a simplified overview of a method in accordance with one embodiment. First, the reflectance spectrum of the window 145 is calibrated against the reflectance spectrum of the reference sample 125 in a manner discussed below in detail, to produce a correction function (block 170 of FIG. 2). This correction function is then stored and the reference sample 125 is removed from the support 100. Then, a production workpiece 120 is placed on the support 100 and the reflectance spectrum of the production workpiece 120 is measured (block 172 of FIG. 2). The measured reflectance spectrum of the production workpiece 120 is then normalized to the response of the viewing window 145 by combining it with the reflectance spectrum of the viewing window 145 by itself (block 174) to produce a normalized reflectance spectrum. This normalized reflectance spectrum is combined with the correction function previously obtained in block 170 to produce the absolute reflectance spectrum of the production workpiece (block 176 of FIG. 2). If the number of production wafers measured thus far or if the elapsed time is less than a predetermined threshold (NO branch of block 177), then the next production wafer is measured in the same manner by replacing the present production wafer on the support with the next production wafer (block 178) and repeating the steps of blocks 172, 174 and 176 (NO branch of block 178). After processing a predetermined number of production wafers in this manner, or after the elapsed time has passed a certain threshold (YES branch of block 177), system drift is accounted for by re-measuring the reflectance spectrum of the viewing window by itself (block 179) and then repeating the foregoing operations (blocks 170, 172, 174, 176, 177 and 178). The cycle is repeated until all the production workpieces have been measured.

Figure 3:
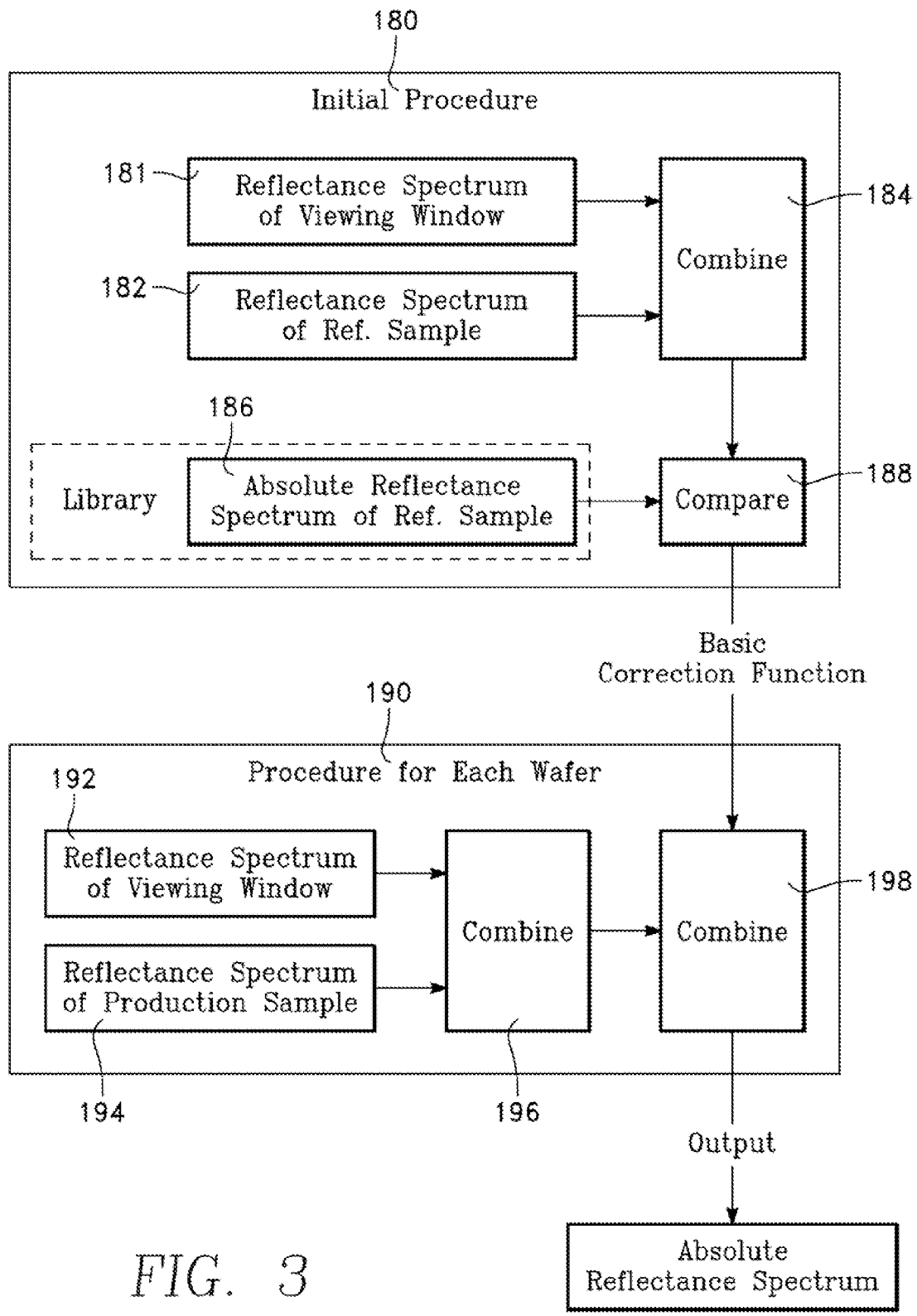
FIG. 3 is a block diagram depicting process and signal flow in an embodiment.

FIG. 3 depicts the flow of processing and data in the embodiment of FIG. 2. Block 180 of FIG. 3 depicts process flow in an initial operation performed once prior to the measurement of a sequence of production workpieces. In block 180, no workpiece 110 is present on the support 100, and the metrology system obtains the reflectance spectrum of the viewing window 145 (block 181 of (FIG. 3), which is then stored in the memory 167. The reference sample 125 is placed on the support 100 and the metrology system obtains the reference sample reflectance spectrum (block 182 of FIG. 3). The spectra of blocks 181 and 182 are combined (block 184) in a manner described below in detail, to produce a combined spectrum. The absolute reflectance spectrum of the reference sample 125 is fetched from the memory 167 (block 186) and compared with the combined spectrum from block 184, and this comparison produces a basic correction function (block 188 of FIG. 3), which is then stored in memory.

Figure 4A:
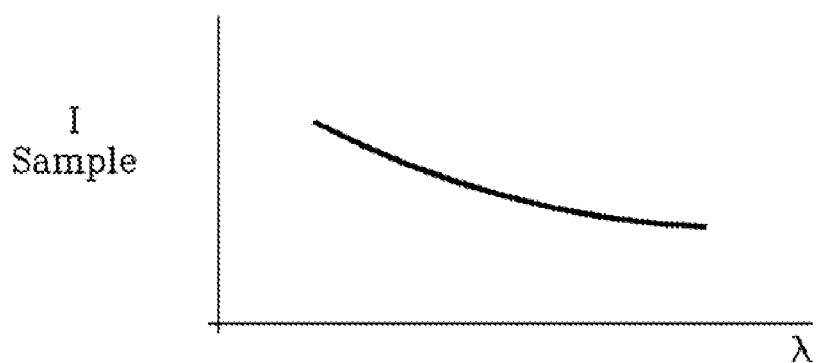
Figure 4B:
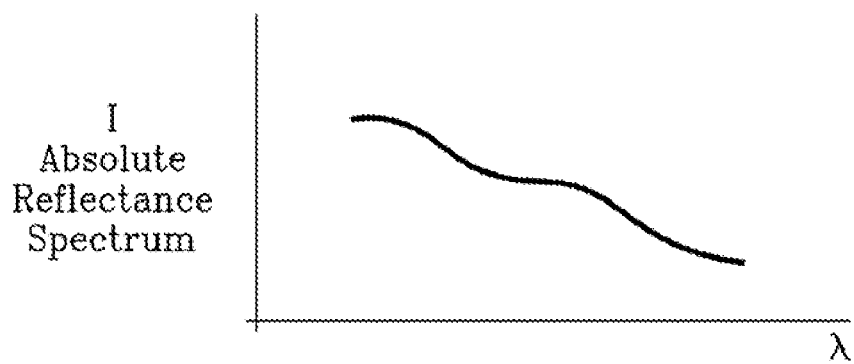
Figure 4C:
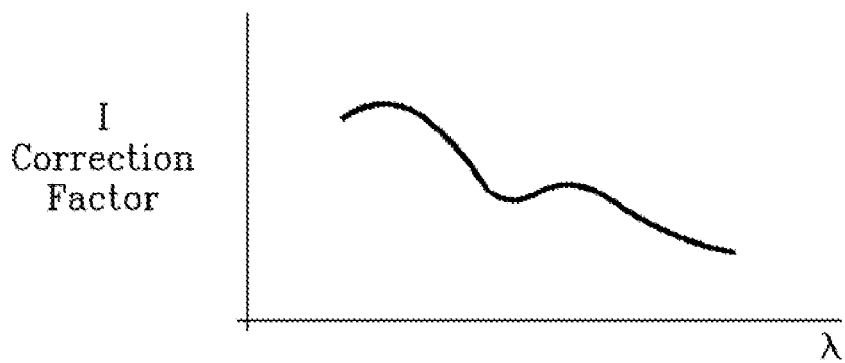

FIGS. 4A, 4B and 4C are graphs qualitatively depicting the relationship between the measured reflectance spectrum of the reference sample 125, as represented by the combined spectrum produced in block 184, and the absolute reflectance spectrum of the reference sample from block 186. The measured spectrum from block 184 is depicted in FIG. 4A, in which the ordinate corresponds to intensity and the abscissa corresponds to wavelength. The absolute reflectance spectrum of the reference sample from block 186 is depicted in FIG. 4B, in which the ordinate corresponds to intensity and the abscissa corresponds to wavelength. The correction function produced at block 188 is depicted roughly in FIG. 4C, in which the ordinate corresponds to intensity and the abscissa corresponds to wavelength. The correction function of FIG. 4C may be obtained by dividing the intensity value at each discrete wavelength in the graph of FIG. 4B by the intensity value at the corresponding wavelength in the graph of FIG. 4A.

Block 190 of FIG. 3 depicts process flow in a step that is repeated for each production workpiece 120 to be measured. Significantly, the reference sample 125 is not measured in block 190. First, the current production workpiece 120 is placed on the support 100 and its reflectance spectrum is obtained by the metrology system (block 192 of FIG. 3). The reflectance spectrum of the viewing window 145 stored from block 181 is obtained from memory (block 194 of FIG. 3). The spectra of blocks 192 and 194 are combined to produce a normalized spectrum (block 196) and this normalized spectrum is combined with the correction function from block 188 to produce the absolute reflectance spectrum of the production workpiece 120 (block 198 of FIG. 3). The process of block 190 is then repeated for the next production workpiece, and this cycle may continue over a number of production workpieces. The reflectance spectrum of the viewing window can be stored in memory in block 181. This stored window reflectance will be combined as in block 196 with the measurements of the next succeeding production workpieces. This is done until another measurement of the viewing window is deemed necessary to be performed to compensate for drift, and the version stored in memory is updated.

Figure 5A:
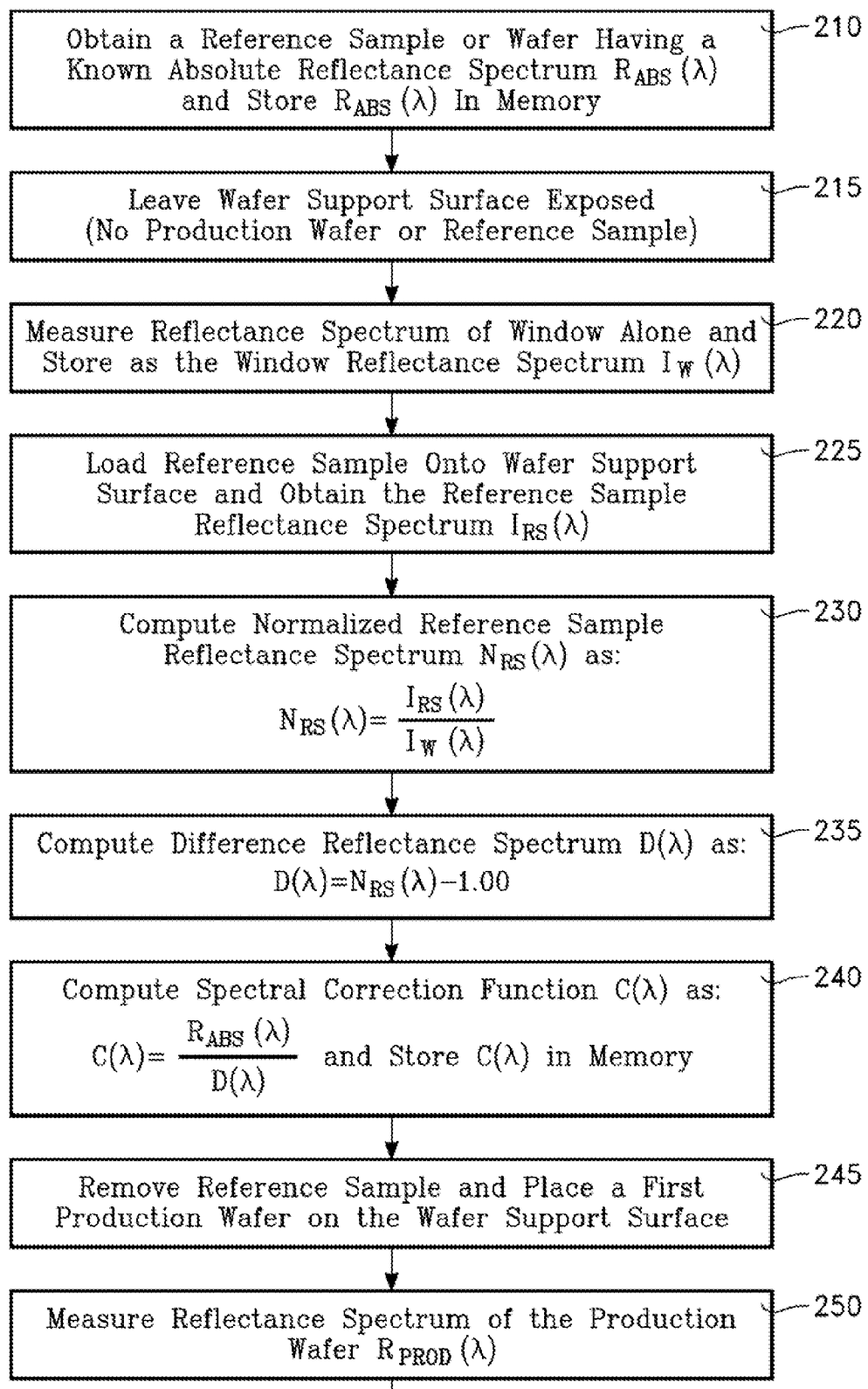
FIGS. 5A and 5B, referred to herein collectively as "FIG. 5", together represent a block diagram depicting in detail a method in accordance with one embodiment.
Figure 5B:
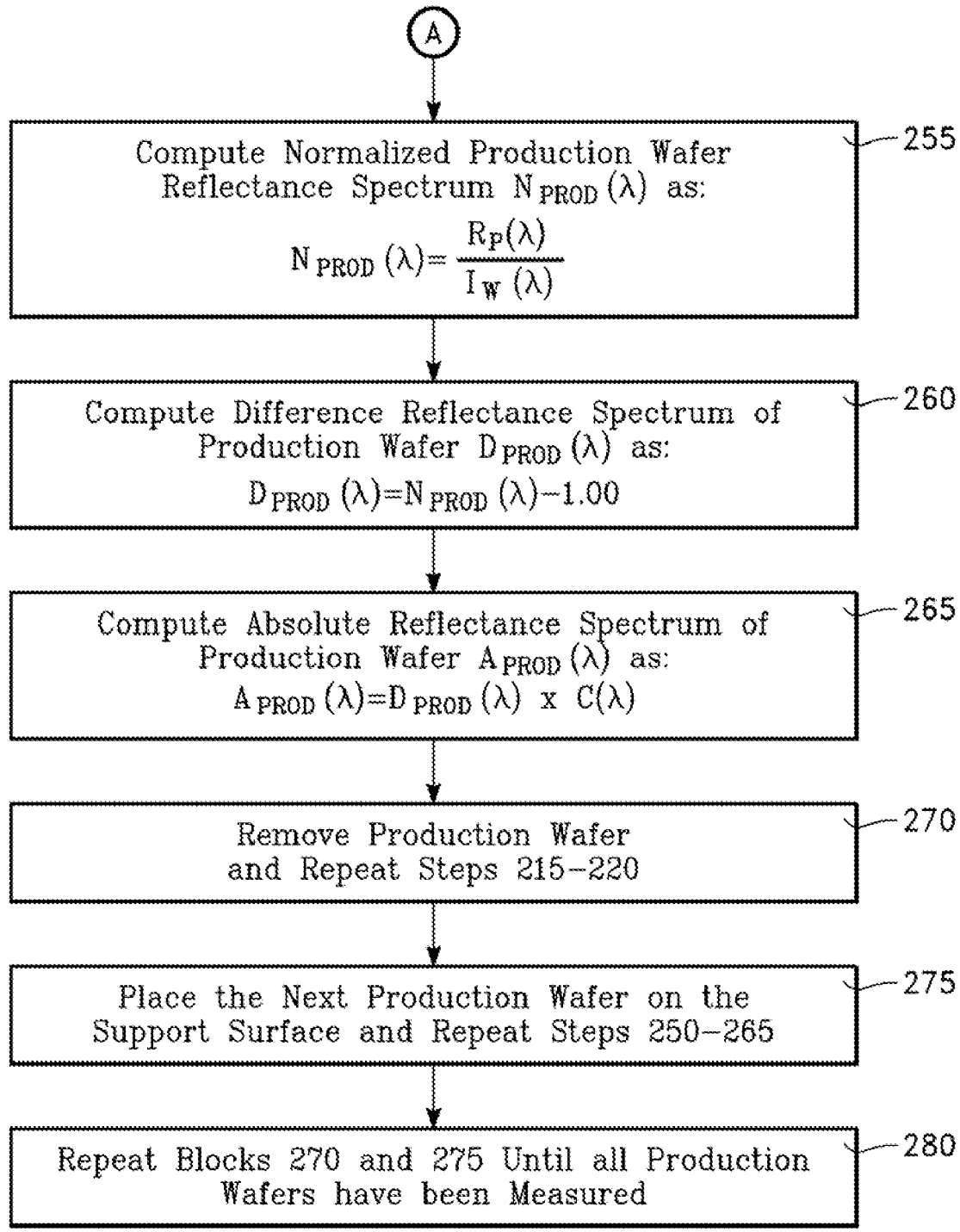
Figure 6A:
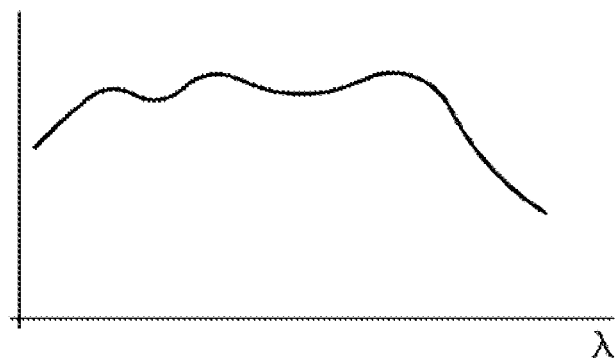

FIG. 5 is a block diagram depicting in detail one embodiment of the process of FIG. 3. In block 210 of FIG. 5, the reference sample 125 is provided to the metrology system of FIG. 1, while the absolute reflectance spectrum, $R_{ABS}(\lambda)$, of the reference sample 125 is obtained from prior experimental results and stored in the memory 167. In block 215 of FIG. 5, the workpiece support surface 105 is left uncovered, no workpiece 110 being held on the support 100, so that the reflectance spectrum of the viewing window 145 is obtained (block 220) and stored in the memory 167 as the window reflectance spectrum $I_w(\lambda)$, where I denotes intensity value as a function of wavelength $\lambda$, and w denotes "window". An exemplary graph of $I_w(\lambda)$ is depicted in FIG. 6A.

Each of the measured spectra discussed here are obtained from light of the source 142 transmitted through the window 145 to the sample or workpiece 110, and reflected back through the window 145 and collected at the light receiver 143. Some of the light collected by the light receiver 143 has been reflected back from the interior surface of the window 145, so that the spectrum sensed by the sensor 160 includes light from the workpiece 110 as well as light reflected from the window 145. When the support surface 105 is left unoccupied, and if the support surface 105 is optically absorbing, then the only spectrum measured is the reflectance spectrum $I_w(\lambda)$ of the window 145 as in block 220 of FIG. 5.

Figure 6B:
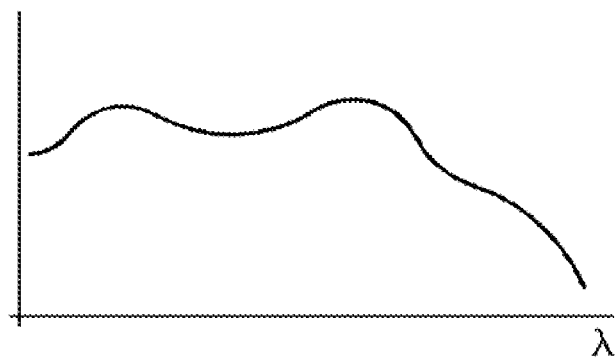

In block 225 of FIG. 5, the reference sample 125 is placed on the support and the sensor 160 obtains the measured reflectance spectrum, $I_{RS}(\lambda)$, of the reference sample 125. The reference sample measured reflectance spectrum $I_{RS}(\lambda)$ is then stored in the memory 167. FIG. 6B depicts an exemplary graph of the measured reference sample reflectance spectrum $I_{RS}(\lambda)$.

In block 230 of FIG. 5, a normalized reference sample reflectance spectrum, $N_{RS}(\lambda)$, is computed by the processor 165 in accordance with the following computation:

$$N_{RS}(\lambda)=[I_{RS}(\lambda)]/[I_w(\lambda)]$$

Figure 6C:
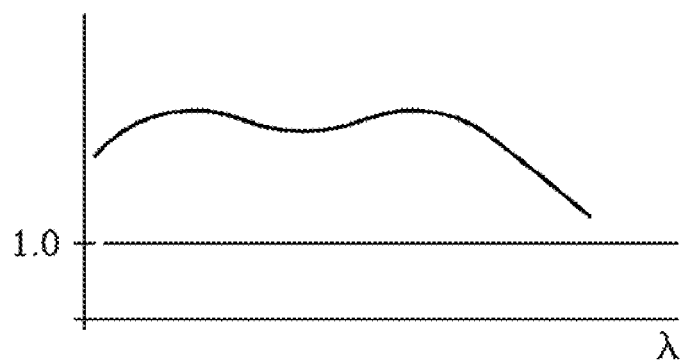

In this computation, one reflectance spectrum, $I_{RS}(\lambda)$, is divided by another, $I_w(\lambda)$. In this description, where two such functions of λ are involved in a division operation, it is understood that the operation is carried out by dividing the intensity value of the one function at each particular wavelength λ by the intensity value of the other function at the same wavelength λ. FIG. 6C depicts an exemplary graph of the normalized reference sample reflectance spectrum, $N_{RS}(\lambda)$, based approximately upon the curves depicted in FIGS. 6A and 6B.

In block 235 of FIG. 5, a difference reflectance spectrum $D_{RS}(\lambda)$ is computed from the normalized spectrum of block 230 in accordance with the following computation:

$$D_{RS}(\lambda)=N_{RS}(\lambda)-1.00$$

In this description, where a function of λ, such as $N_{RS}(\lambda)$, is involved in a subtraction by 1.00, the operation is carried out by subtracting a value of 1.00 from each intensity value of the function at each value of λ.

Figure 6D:
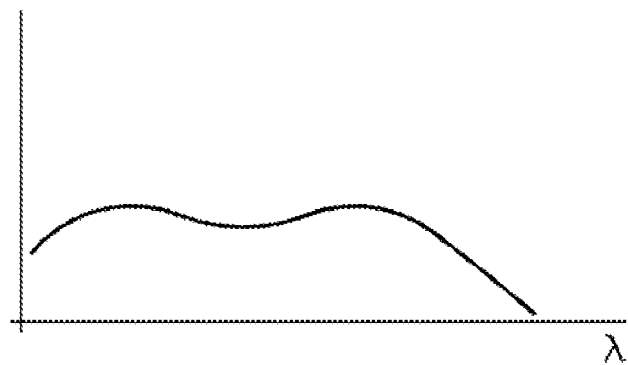

The contribution of the reflected light from the window 145 to the normalized spectrum $N_{RS}(\lambda)$ is unity (i.e., 1.00) at all wavelengths, due to the normalization procedure of block 230, assuming there is no intervening drift in the light source 142, for example. Therefore, the contribution of the reference sample is isolated by the subtraction of unity from the normalized spectrum $N_{RS}(\lambda)$ in block 235. FIG. 6D depicts an exemplary graph of the reference sample difference reflectance spectrum, $D_{RS}(\lambda)$ based roughly upon the curve depicted in FIG. 6C. FIG. 6D depicts the shift of the curve of FIG. 6C by unity along the ordinate (intensity axis).

In block 240 of FIG. 5, the correction function $C(\lambda)$ is computed by the processor 165 in accordance with the computation:

$$C(\lambda)=[R_{ABS}(\lambda)]/[D_{RS}(\lambda)]$$

Figure 6E:
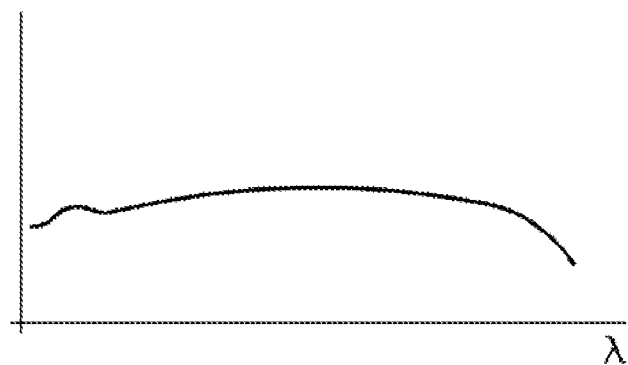

The processor 165 stores the correction function $C(\lambda)$ in the memory 167. FIG. 6E depicts a graph of the correction function $C(\lambda)$ based upon the curves of FIGS. 6A and 6D.

The sequence of blocks 210 through 240 of FIG. 5 constitute the initial process of block 180 of FIG. 3. The cyclically repeated process of block 190 of FIG. 3 begins with block 245 of FIG. 5.

Figure 6F:
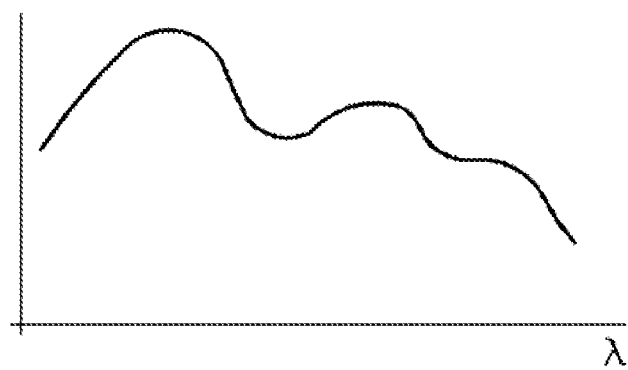

In block 245 of FIG. 5, the reference sample 125 is removed from the support 100 and a first production workpiece 120 is placed on the support. In block 250, the reflectance spectrum of the production workpiece, $R_{PROD}(\lambda)$, is captured by the sensor 160 and stored by the processor 165 in the memory 167. An arbitrary example of $R_{PROD}(\lambda)$ is depicted in the graph of FIG. 6F.

In block 255, a normalized reflectance spectrum of the production workpiece is computed in accordance with the computation:

$$N_{PROD}(\lambda)=[R_{PROD}(\lambda)]/[I_w(\lambda)]$$

Figure 6G:
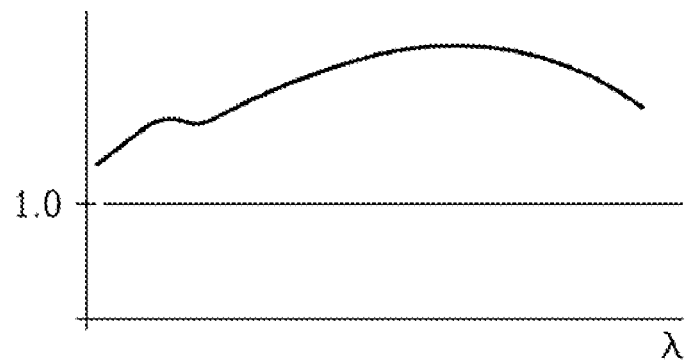

The normalized reflectance spectrum $N_{PROD}(\lambda)$ is the production workpiece reflectance spectrum normalized to the window reflectance spectrum. FIG. 6G depicts a graph of $N_{PROD}(\lambda)$ approximately based upon the curves of FIGS. 6F and 6A.

In block 260 of FIG. 5, a difference reflectance of the production workpiece, $D_{PROD}(\lambda)$, is computed by the processor 165 in accordance with the computation:

$$D_{PROD}(\lambda)=N_{PROD}(\lambda)-1.00$$

Figure 6H:
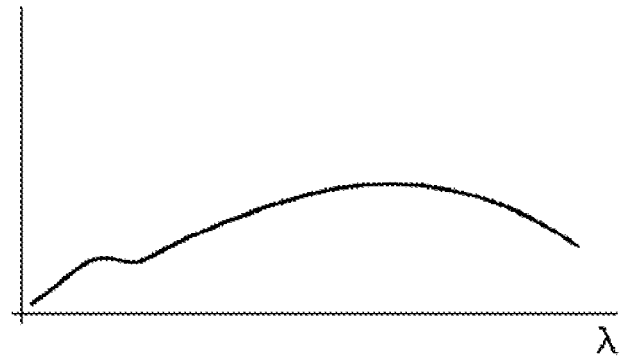

This step is analogous to the computation of block 235 of FIG. 5, in that it isolates the spectrum of the production workpiece from the effects window 145. FIG. 6H is a graph of $D_{PROD}(\lambda)$ based upon the curve of FIG. 6G.

In block 265, the correction function $C(\lambda)$ from block 240 is fetched from the memory 167, and the production workpiece absolute reflectance, $A_{PROD}(\lambda)$, is computed by the processor 165 in accordance with the computation:

$$A_{PROD}(\lambda)=D_{PROD}(\lambda) \cdot C(\lambda)$$

Figure 6I:
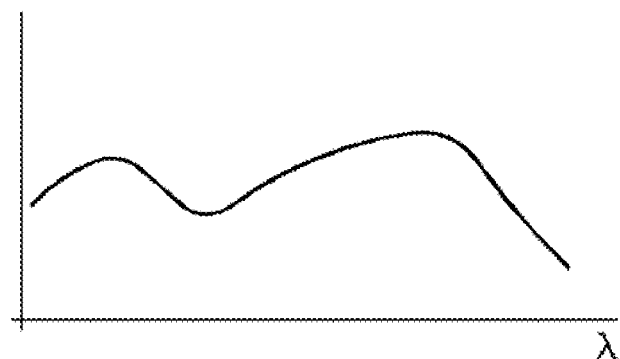

In this description, where two functions of λ, namely $D_{PROD}(\lambda)$ and $C(\lambda)$, are involved in a multiplication operation, it is understood that the operation is carried out by multiplying the intensity value of the one function at each particular wavelength λ by the intensity value of the other function at the same wavelength λ. The absolute reflectance spectrum $A_{PROD}(\lambda)$ of the production workpiece is output as a final result to other metrology apparatus for computation of a surface characteristic of interest, such as thin film thickness, or the height or width of a periodic structural feature. FIG. 6I depicts a graph of the absolute reflectance spectrum $A_{PROD}(\lambda)$ based approximately upon the curves of FIGS. 6H and 6E.

In block 270, a determination is made whether the number of production wafers that have been measured since the window reflectance was first obtained, or the elapsed time, has reached a predetermined threshold, beyond which system drift becomes a significant risk. This number is estimated from prior system performance and observation of drift. If the number of production wafers processed (or the elapsed time) is less than the threshold (NO branch of block 270), then the next production wafer is placed on the support (block 275) and the process repeats the cycle beginning with block 250. Otherwise, if the threshold number of production wafers or the elapsed time threshold has been reached (YES branch of block 270), the process returns to block 215 in order to obtain a new window reflectance spectrum and performs the subsequent blocks in order to obtain a new correction factor in block 240.

While the foregoing is directed to embodiments of the present invention, other and further embodiments of the invention may be devised without departing from the basic scope thereof, and the scope thereof is determined by the claims that follow.

What is claimed is:

1. A method of measuring the reflectance spectrum of a workpiece using an optical sensing apparatus having a viewing window facing a workpiece support surface, comprising:
    computing a correction function by combining together (A) a predetermined reflectance spectrum of a reference sample and (B) a measured reflectance spectrum of said reference sample that has been (a) measured through said viewing window and (h) normalized with a reflectance spectrum of said viewing window;
    measuring through said viewing window a reflectance spectrum of a workpiece, normalizing said reflectance spectrum of the workpiece with the reflectance spectrum of said viewing window, and computing a reflectance spectrum of the workpiece by combining the normalized workpiece reflectance spectrum with said correction function.

2. The method of claim 1 further comprising obtaining the reflectance spectrum of said viewing window by collecting light reflected internally in said optical apparatus from said viewing window.

3. The method of claim 2 wherein said obtaining a reflectance spectrum of said viewing window further comprises refraining from placing a workpiece on said support surface while providing said support surface as a non-reflective surface.

4. The method of claim 1 further comprising normalizing said measured reflectance spectrum of said reference sample by combining said measured reflectance spectrum of said reference sample with the reflectance spectrum of said viewing window.

5. The method of claim 4 wherein said combining said measured reflectance spectrum of said reference sample with the reflectance spectrum of said viewing window comprises performing a division between said measured reflectance spectrum of said reference sample and the reflectance spectrum of said viewing window.

6. The method of claim 5 wherein said performing a division between said measured reflectance spectrum of said reference sample and the reflectance spectrum of said viewing window comprises dividing said measured reflectance spectrum of said reference sample by the reflectance spectrum of said viewing window.

7. The method of claim 4 wherein said normalizing the measured reflectance spectrum of said reference sample further comprises subtracting from said normalized reflectance spectrum an intensity value of unity or 1.00.

8. The method of claim 1 wherein said combining said predetermined reflectance spectrum and the normalized reflectance spectrum of said reference sample comprises performing a division between said predetermined reflectance spectrum of said reference sample and the normalized reflectance spectrum of said reference sample.

9. The method of claim 8 wherein said performing a division between said measured reflectance spectrum of said reference sample and the reflectance spectrum of said viewing window comprises dividing said measured reflectance spectrum of said reference sample by the reflectance spectrum of said viewing window.

10. The method of claim 2 further comprising remeasuring the reflectance spectrum of said viewing window after either: (a) obtaining the reflectance spectra of a predetermined number of said succession of production workpieces or (b) an elapsed time has exceeded a predetermined threshold.

11. The method of claim 10 wherein said obtaining a reflectance spectrum of said viewing window further comprises refraining from placing a workpiece on said support surface while providing said support surface as a non-reflective surface.

12. The method of claim 1 wherein said normalizing the workpiece reflectance spectrum comprises combining said workpiece reflectance spectrum with the reflectance spectrum of said viewing window.

13. The method of claim 12 wherein said combining said workpiece reflectance spectrum with the reflectance spectrum of said viewing window comprises performing a division between said workpiece reflectance spectrum and the reflectance spectrum of said viewing window.

14. The method of claim 13 wherein said performing a division between said workpiece reflectance spectrum and the reflectance spectrum of said viewing window comprises dividing said workpiece reflectance spectrum by the reflectance spectrum of said viewing window.

15. The method of claim 12 wherein said normalizing the workpiece reflectance spectrum further comprises subtracting from said normalized reflectance spectrum of said workpiece an intensity value of unity or 1.00.

16. The method of claim 1 wherein said combining normalized reflection spectrum of said workpiece and said correction function comprises performing a multiplication of said normalized reflection spectrum of said workpiece by said correction function.

17. A method of performing spectrographic workpiece metrology through an optical viewing window, comprising:
calibrating the viewing window against a reference sample of a predetermined reflectance spectrum to produce a normalized reflectance spectrum of the reference sample;
combining the normalized reflectance spectrum with the predetermined reflectance spectrum to produce a correction factor;
measuring reflectance spectra of a workpiece through said window and normalizing said reflectance spectra of the workpiece against the viewing window reflectance spectrum to produce a normalized workpiece reflectance spectrum; and
transforming the normalized workpiece reflectance spectrum using said correction factor.

* * * * *